US007628066B2

(12) United States Patent
Deng et al.

(10) Patent No.: US 7,628,066 B2
(45) Date of Patent: Dec. 8, 2009

(54) APPARATUS AND METHOD FOR EVALUATING PEEL ADHESION

(75) Inventors: Meng Deng, Branchburg, NJ (US); Robert Nering, Delaware, NJ (US)

(73) Assignee: Ethicon, Inc., Somerville, NJ (US)

( * ) Notice: Subject to any disclaimer, the term of this patent is extended or adjusted under 35 U.S.C. 154(b) by 191 days.

(21) Appl. No.: 11/678,000

(22) Filed: Feb. 22, 2007

(65) Prior Publication Data

US 2008/0202254 A1 Aug. 28, 2008

(51) Int. Cl.
*G01N 19/04* (2006.01)
*G01N 3/08* (2006.01)
(52) U.S. Cl. ...................... 73/150 A; 73/827
(58) Field of Classification Search ............... 73/150 A, 73/827
See application file for complete search history.

(56) References Cited

U.S. PATENT DOCUMENTS 2,473,517 A * 6/1949 Freedman ................. 73/150 A (Continued)

FOREIGN PATENT DOCUMENTS

AU 581511 11/1986

(Continued)

OTHER PUBLICATIONS

"Definitions and Keywords" Dec. 7, 2004. Accessed on Oct. 21, 2008. <http://web.archive.org/web/20041207064414/http://instruct1.cit.cornell.edu/Courses/virtual_lab/popups/defKeywd.html>.*

(Continued)

*Primary Examiner*—Lisa M Caputo
*Assistant Examiner*—Jonathan Dunlap
(74) *Attorney, Agent, or Firm*—Roberts Mlotkowski Safran & Cole, P.C.

(57) ABSTRACT

An apparatus for evaluating the peel adhesion of a test specimen to a substrate. The apparatus includes a base plate having a surface for receiving the substrate; a substrate clamping plate for securing the substrate to the substrate receiving surface of the base plate; a test specimen clamping mechanism, the test specimen clamping mechanism having a first end for securing a first end of the test specimen thereto and a second end; and a pivotable linkage, the pivotable linkage having a first end for connecting to the second end of the test specimen clamping mechanism and a second end pivotably mounted to an adaptor, the adaptor in communication with a source of tensile force, wherein the source of tensile force is applied through or via the adaptor to draw the pivotable linkage and test specimen clamping mechanism away from the base plate and peel the test specimen away from the substrate. Also disclosed is a method for evaluating the peel adhesion of a test specimen to a substrate.

17 Claims, 10 Drawing Sheets

U.S. PATENT DOCUMENTS

| | | | |
|---|---|---|---|
| 2,751,784 | A | 6/1956 | S. Gershberg |
| 2,989,865 | A | 6/1961 | Belfour |
| 3,019,644 | A * | 2/1962 | Mancini .................... 73/150 A |
| 3,564,911 | A | 2/1971 | Slemmons et al. |
| 4,895,028 | A | 1/1990 | Mayer |
| 6,158,645 | A * | 12/2000 | Sakamoto et al. ........ 228/110.1 |
| 6,370,948 | B2 * | 4/2002 | Arrington et al. ......... 73/150 A |
| 6,478,264 | B1 | 11/2002 | Nelson et al. |
| 6,553,843 | B1 | 4/2003 | Courtade |
| 6,733,774 | B2 | 5/2004 | Stimmeder |
| 6,762,336 | B1 | 7/2004 | MacPhee |
| 2006/0237128 | A1 | 10/2006 | Watanabe |

FOREIGN PATENT DOCUMENTS

| | | | |
|---|---|---|---|
| CA | 2 490 600 | | 6/2006 |
| GB | 1 346 761 | | 2/1974 |
| JP | 57044834 | A * | 3/1982 |
| WO | 2004064878 | | 8/2004 |

OTHER PUBLICATIONS

Imada, Co. "Force Gauge Attachment". Sep. 2005. Acessed on Oct. 21, 2008. <http://www.forcegauge.net/catalog/products/specification/fc21uq-e.pdf>.*

K. Bundy, "An Improved Peel Test Method For Measurement of Adhesion to Biomaterials", Journal of Materials Science: Materials in Medicine, 11 (2000) pp. 517-521.

* cited by examiner

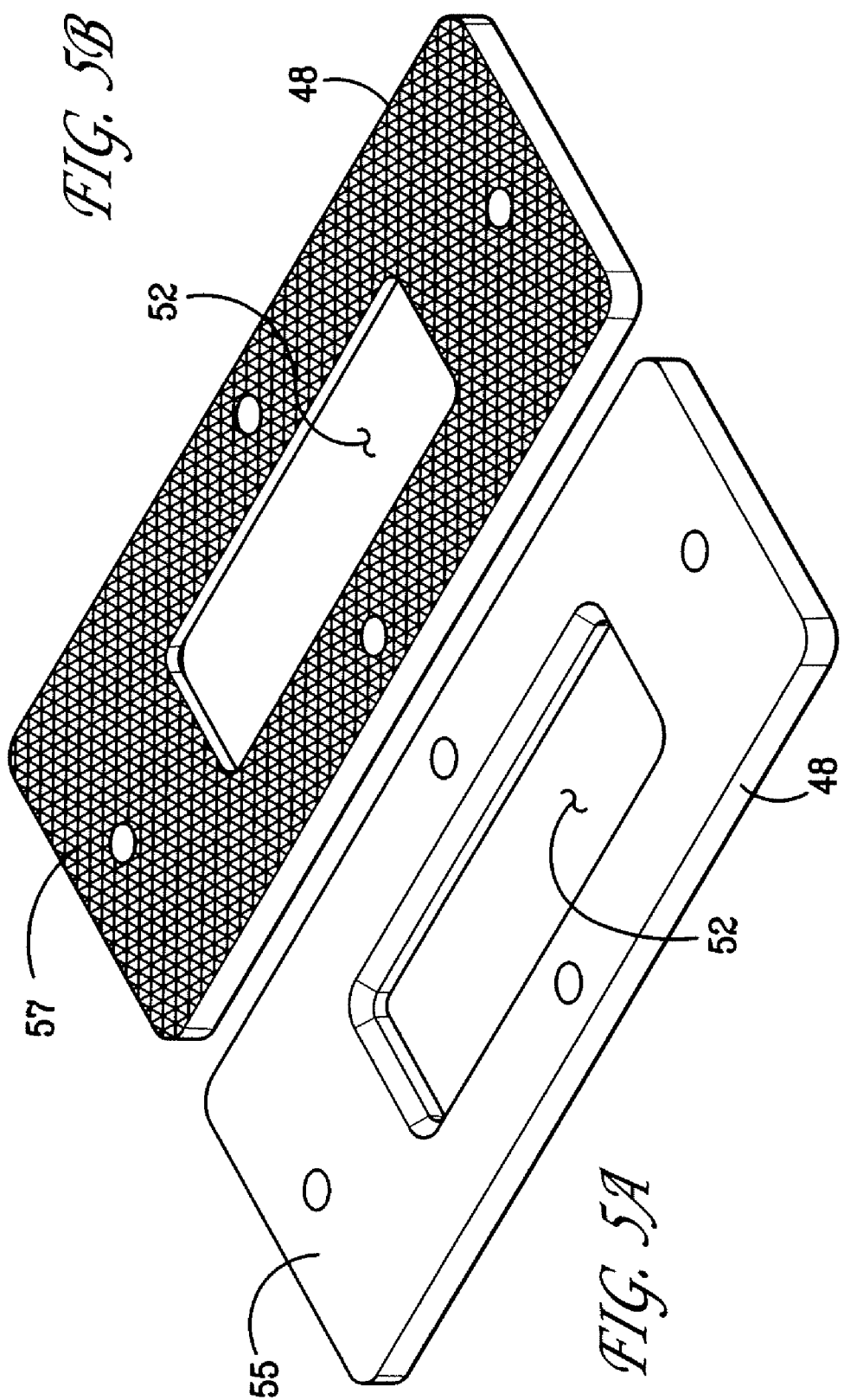

APPARATUS AND METHOD FOR EVALUATING PEEL ADHESION

FIELD

An apparatus and method for the testing of peel adhesion of test specimens is disclosed.

BACKGROUND

The control of bleeding as well as the sealing of air and various bodily fluids is essential and critical in surgical procedures to minimize blood loss, to seal tissue and organ structures, to reduce post-surgical complications, and to shorten the duration of the surgery in the operating room.

In an effort to provide dressings with enhanced hemostatic and tissue sealing and adhering properties, therapeutic agents, including, but not limited to, thrombin, fibrin and fibrinogen have been combined with dressing carriers or substrates, including gelatin-based carriers, polysaccharide-based carriers, glycolic acid or lactic acid-based carriers and a collagen matrix. Examples of such dressings are disclosed in U.S. Pat. Nos. 6,762,336, 6,733,774 and PCT Publication No. WO 2004/064878 A1.

In order to evaluate the efficacy of dressings with enhanced hemostatic, tissue sealing and adhering properties, it is desirable to quantify the peel adhesion properties of a dressing. Peel adhesion testing is a well established methodology in industrial applications involving tapes, adhesives and the like. It has also been employed to a limited extent in the biomaterials field. Various standard methods for conducting peel tests are available including T-peel, cleavage peel, climbing drum and floating roller techniques.

Although the aforementioned tests have many important industrial uses, they are not particularly well suited when the peel adhesion testing involves the measurement of soft tissue adherence. For this purpose standard techniques present certain disadvantages. For example, the status of the soft tissue/dressing interface may be rather unstable and susceptible to dehydration and other changes, while at the same time the delay between surgical removal of the specimen and the actual conduct of the peel test may be substantial.

Additionally, a variable angle between the peeling force and the substrate in some of the standard tests available today presents a complication from a biomechanical standpoint. Accordingly, it would be desirable to maintain a substantially constant angle throughout the test. Tests carried out heretofore utilizing the winding drum method have produced results having wide variability. In conventional winding drum testing, one aluminum strip of the test specimen is first secured to a rigid bar as a backing and the bar is suspended by one of its ends from an upper tensile-applying point of the test machine. A turned-out end of the other aluminum strip is tucked and attached within a slot of a drum having substantial weight. Flexible bands around the flanges of the drum are brought downward and attached by a yoke to an attachment point in the laboratory floor. The upper tensile-applying point has associated therewith a force registering means.

K. Bundy, in "An Improved Peel Test Method for Measurement of Adhesion to Biomaterials," *Journal of Materials Science: Materials in Medicine,* 11 (2000) 517-521, proposes a portable peel-testing instrumentation for testing adherence of soft tissues to biomaterials. It is said to maintain a 900 angle between peel and substrate, simplifying the determination of applied normal forces when separating tissue layers from material surfaces. The instrument has been reported to have been used to test adhesion of tape to a biomaterial surface, assess strength of tissue adhesives and measure adhesion of subcutaneous tissue to orthopedic biomaterials. However, in the method proposed, the tissue is the moving part while the substrate is fixed. As the tissue stretches during testing, error is introduced into the calculation of peel force. In fact, the data presented reveals a rather large variation.

U.S. Pat. No. 2,989,865 proposes an apparatus for testing the peel strength of joints that comprises improvements in the apparatus and method for testing whereby an end of one of two members so joined (usually thin strips of aluminum) is secured to a winding drum and peeled from the other member by winding progressively on the drum, the force required for such peeling being continuously registered.

U.S. Patent Publication No. 2006/0237128 proposes a method of bonding two materials directly with each other, at least one of which is made of a plastic material, which method is applicable to bonding two materials, with no need to use any bonding agent and without allowing the materials to be exposed to high temperature and/or high pressures. In this method in which a first member made of a plastic material and a second member are bonded together, one surface of the first member to be bonded with the second member is irradiated with energy rays having a quantity of energies not lower than 4 eV, followed by directly bonding the first and second members together without any bonding agent being used. A method of conducting a peel strength test at a right angle to determine the adhesive strength is proposed in U.S. Patent Publication No. 2006/0237128.

Despite these advances in the art, there remains a need for an apparatus and method for evaluating the peel adhesion of a test specimen to a substrate.

SUMMARY

In one aspect, provided is an apparatus for evaluating the peel adhesion of a test specimen to a substrate. The apparatus includes a base plate having a surface for receiving the substrate, a substrate clamping plate for securing the substrate to the substrate receiving surface of the base plate, a test specimen clamping mechanism, the test specimen clamping mechanism having a first end for securing a first end of the test specimen thereto and a second end and a pivotable linkage, the pivotable linkage having a first end for connecting to the second end of the test specimen clamping mechanism and a second end pivotably mounted to an adaptor, the adaptor in communication with a source of tensile force, wherein the source of tensile force is applied through or via the adaptor to draw the pivotable linkage and test specimen clamping mechanism away from the base plate and peel the test specimen away from the substrate.

In another aspect, provided is a method of evaluating the peel adhesion of a test specimen to a substrate. The method includes the steps of placing a first surface of the substrate on a base plate having a surface for receiving the substrate, securing the substrate to the substrate receiving surface of the base plate, securing a first end of a test specimen clamping mechanism to a first end of the test specimen, affixing a first surface of the test specimen to the second surface of the substrate, affixing a first end of a pivotable linkage to a second end of the test specimen clamping mechanism, the second end of the pivotable linkage pivotably mounted to an adaptor, the adaptor in communication with a source of tensile force and applying a tensile force through or via the adaptor to draw the pivotable linkage and test specimen clamping mechanism away from the base plate and peel the first surface of the test specimen away from the second surface of the substrate.

These and other features will be apparent from the detailed description taken with reference to accompanying drawings.

BRIEF DESCRIPTION OF THE DRAWINGS

The invention will now be described in more detail with reference to the forms herein disclosed, given only by way of example, and with reference to the accompanying drawings, in which:

FIG. 5A shows a top perspective view of a substrate clamping plate for use in an apparatus for evaluating the peel adhesion of a test specimen to a substrate, as disclosed herein;

FIG. 5B shows a bottom perspective view of the substrate clamping plate of FIG. 5A, as disclosed herein;

DETAILED DESCRIPTION

Definitions

Unless defined otherwise, all technical and scientific terms used herein are intended to have the same meaning as is commonly understood by one of ordinary skill in the relevant art.

As used herein, the singular forms "a," "an," and "the" include the plural reference unless the context clearly dictates otherwise.

Various aspects will now be described with reference to specific forms selected for purposes of illustration. It will be appreciated that the spirit and scope of the apparatus and method disclosed herein is not limited to the selected forms.

Moreover, it is to be noted that the figures provided herein are not drawn to any particular proportion or scale, and that many variations can be made to the illustrated forms. Reference is now made to FIGS. 1-14, wherein like numerals are used to designate like parts throughout.

In one form, provided is an apparatus for evaluating the peel adhesion of a test specimen to a substrate. The apparatus includes a base plate having a surface for receiving the substrate, a substrate clamping plate for securing the substrate to the substrate receiving surface of the base plate, a test specimen clamping mechanism, the test specimen clamping mechanism having a first end for securing a first end of the test specimen thereto and a second end and a pivotable linkage, the pivotable linkage having a first end for connecting to the second end of the test specimen clamping mechanism and a second end pivotably mounted to an adaptor, the adaptor in communication with a source of tensile force, wherein the source of tensile force is applied to the adaptor to draw the pivotable linkage and test specimen clamping mechanism away from the base plate and peel the test specimen away from the substrate.

Figure 1:
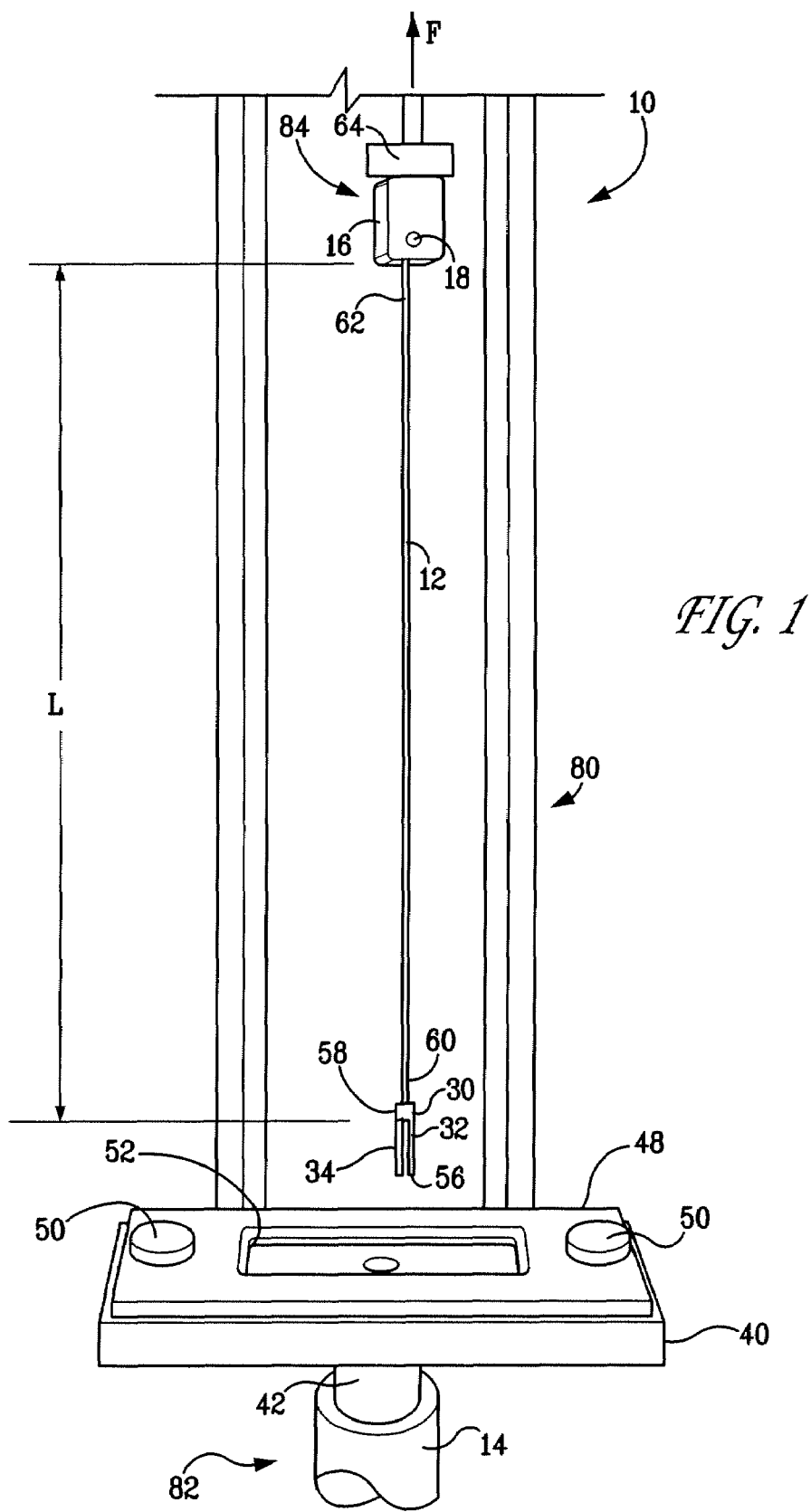
FIG. 1 shows an apparatus for evaluating the peel adhesion of a test specimen to a substrate, as disclosed herein.
Figure 2:
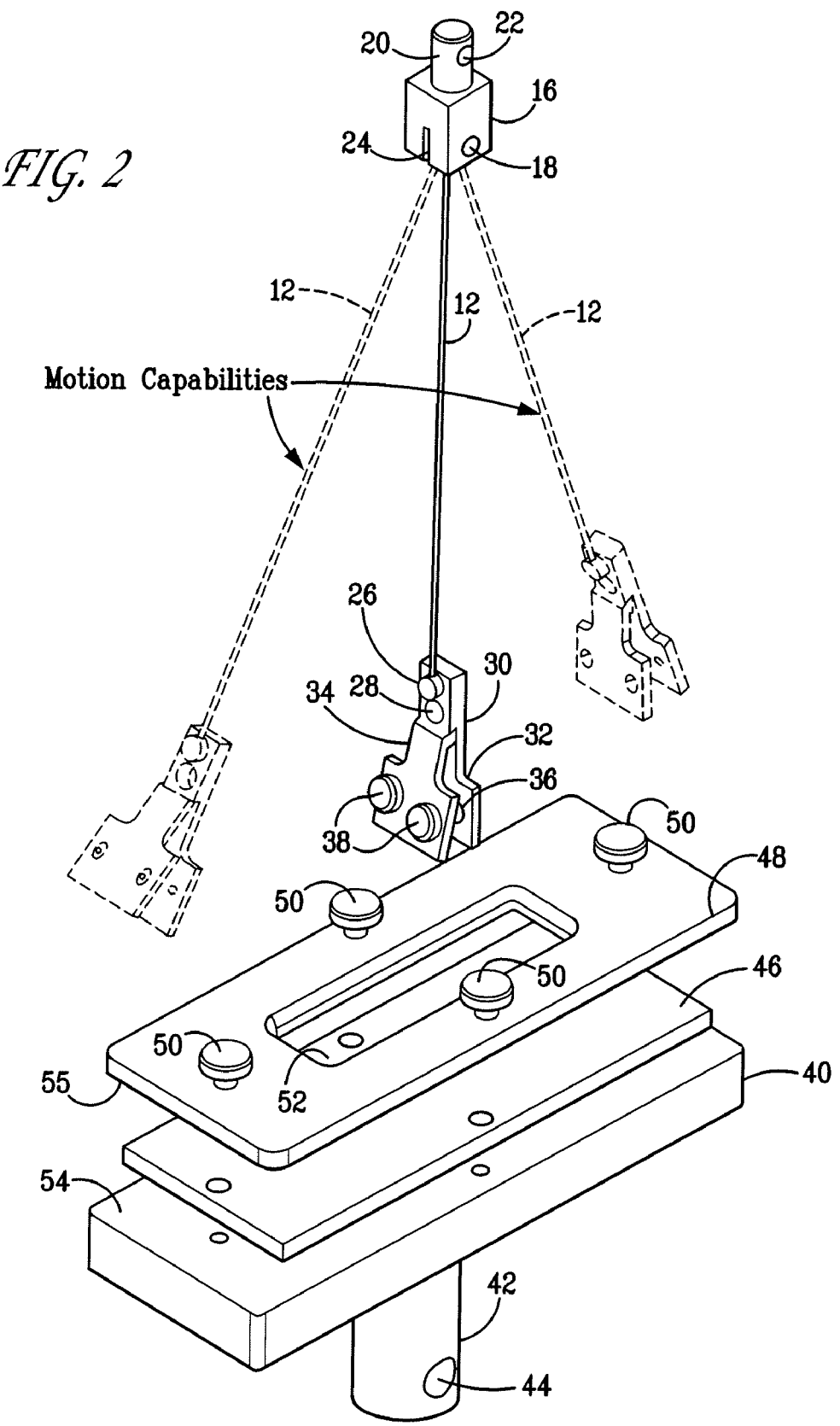
FIG. 2 shows a perspective view of selected fixtures of the apparatus for evaluating the peel adhesion of a test specimen to a substrate disclosed herein, showing the motion capabilities provided thereby.
Figure 6:
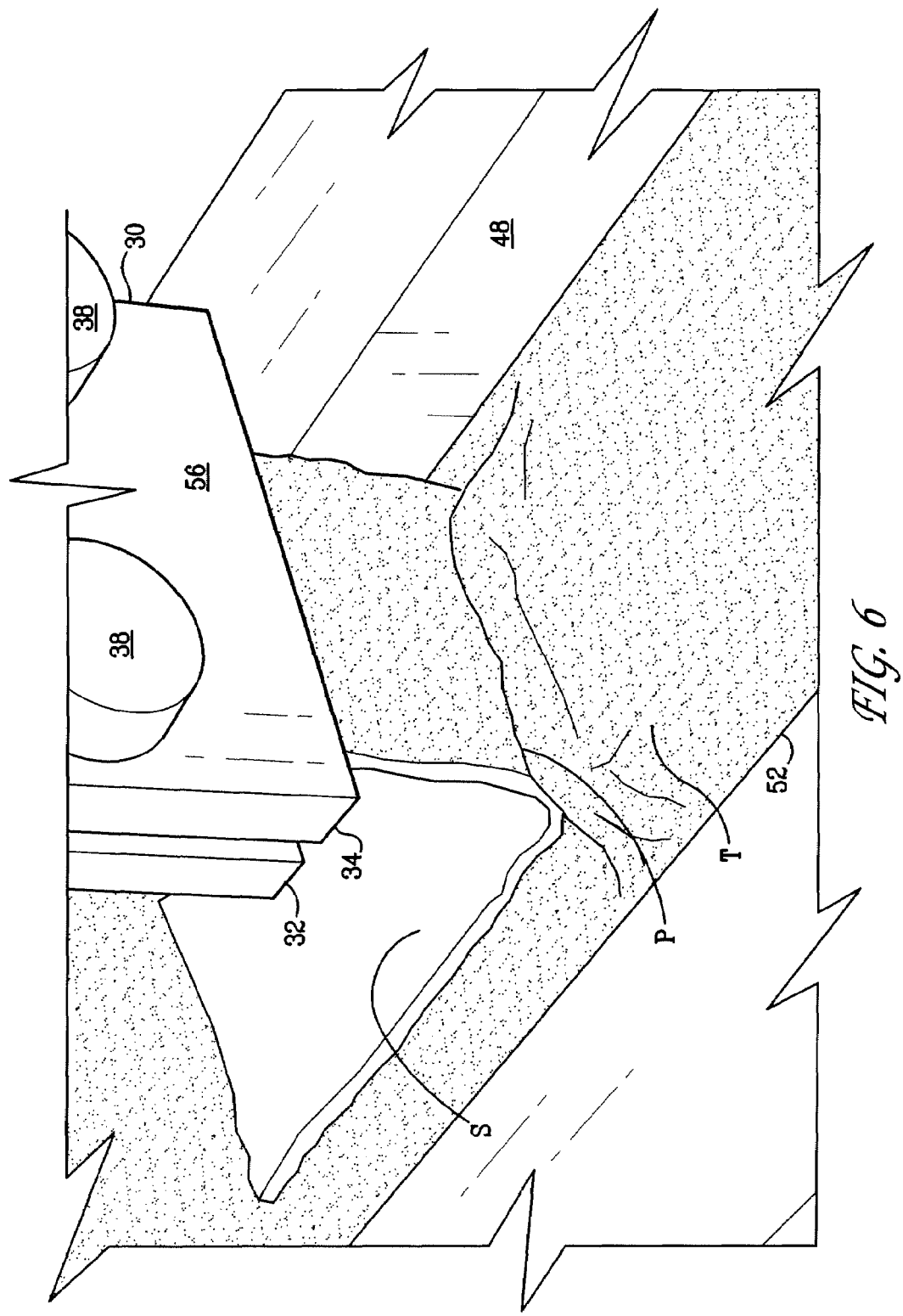
FIG. 6 depicts a portion of the apparatus for evaluating the peel adhesion of a test specimen to a substrate, in use, wherein a test specimen is being peeled from a substrate.

Referring now to FIGS. 1, 2 and 6, an apparatus 10 for evaluating the peel adhesion of a test specimen S to a substrate T is shown. The apparatus 10 includes a base plate 40 having a surface 54 for receiving the substrate T. Base plate 40 may also include mounting post 42 and locking pin orifice 44, for securing base plate 40 to tensile test load frame 14 of tensile testing machine 80. Optionally, substrate T may be placed upon media slide 46 prior to being positioned upon substrate receiving surface 54 of base plate 40. A substrate clamping plate 48, having a window 52, is provided for securing substrate T to the substrate receiving surface 54 of base plate 40. In one form, a plurality of clamping plate screws 50 may be provided for securing substrate clamping plate 48 and substrate T to substrate receiving surface 54 of base plate 50.

Figure 3:
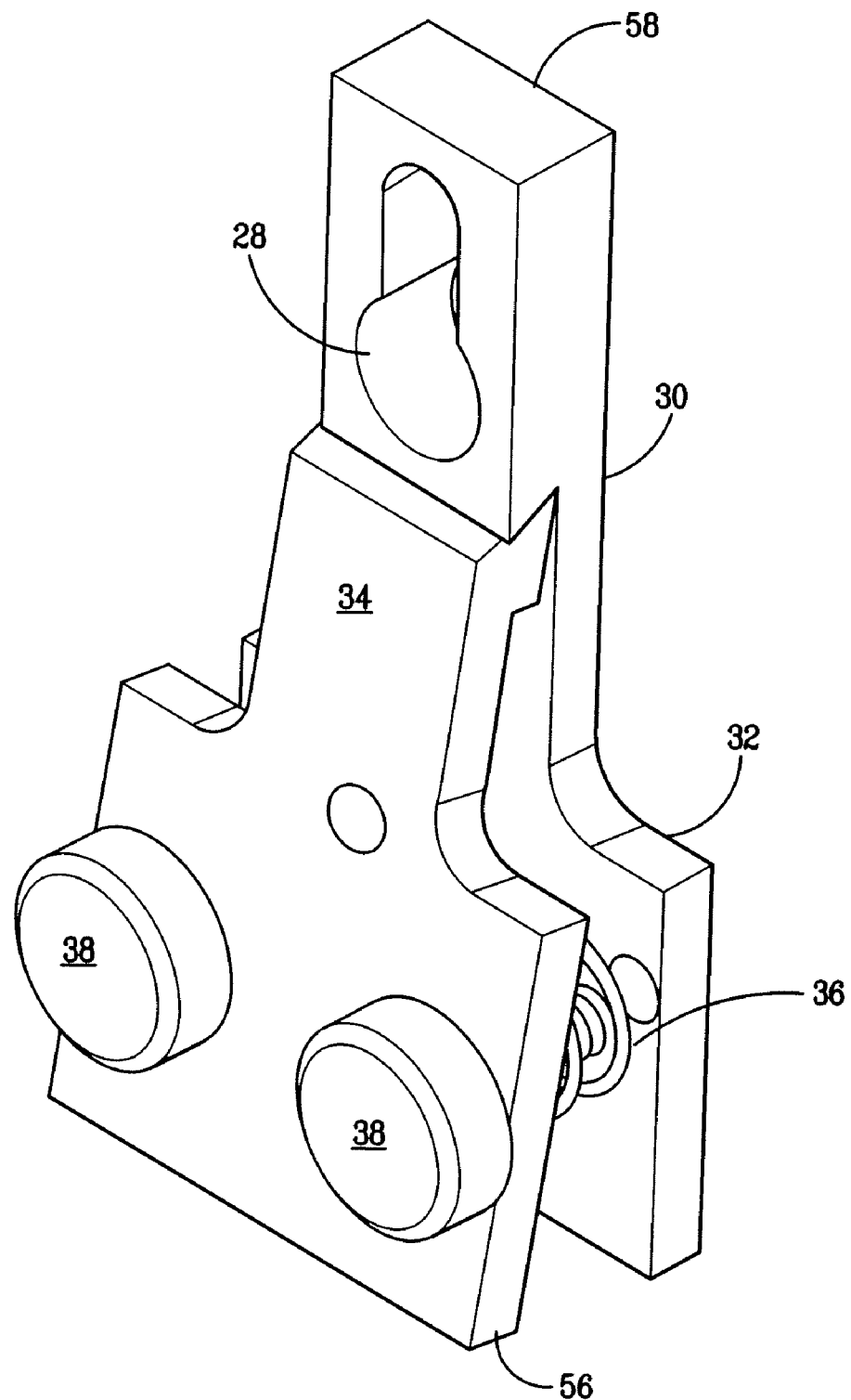
FIG. 3 shows a form of a specimen clamping mechanism for use in an apparatus for evaluating the peel adhesion of a test specimen to a substrate, as disclosed herein.

To secure test specimen S, a test specimen clamping mechanism 30 is provided. As shown in FIGS. 2, 3 and 6, test specimen clamping mechanism 30 includes a first end 56 for securing a first end of the test specimen S and a second end 58. Second end 58 of test specimen clamping mechanism 30 is attached to a pivotable linkage 12. Test specimen clamping mechanism 30 includes a stationary clamping jaw 32 and a moveable clamping jaw 34. In operation, biasing means 36, which may be a pair of coil springs, as shown, urges stationary clamping jaw 32 away from moveable clamping jaw 34 to enable a test specimen S to easily be inserted therebetween. At least one test specimen clamping screw 38 may be provided for securing stationary clamping jaw 32 to moveable clamping jaw 34.

Figure 4A:
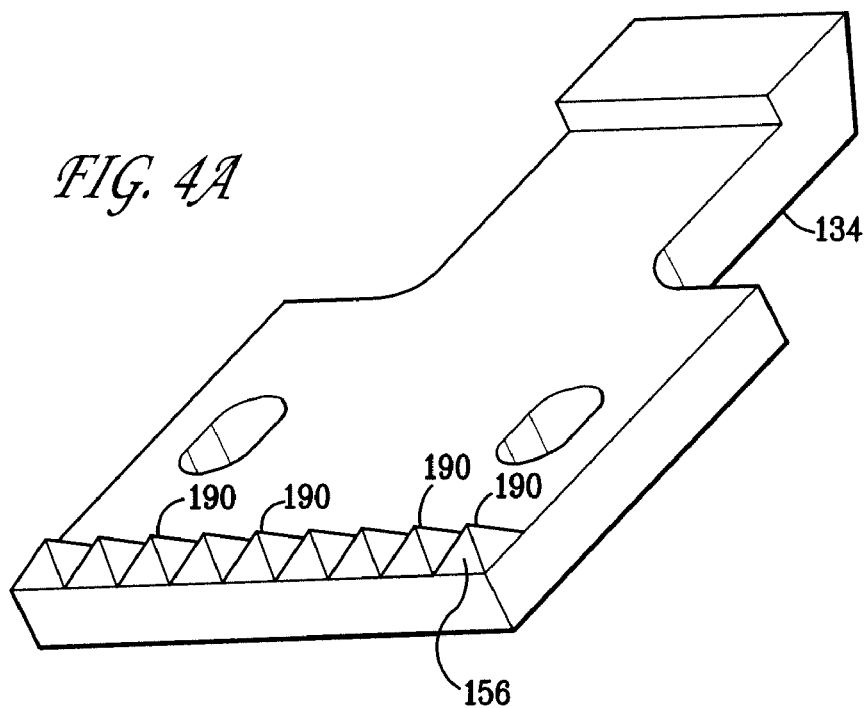
FIG. 4A shows another form of a moveable clamping jaw of a specimen clamping mechanism for use in an apparatus for evaluating the peel adhesion of a test specimen to a substrate, as disclosed herein.

Referring now to FIG. 4A, an alternate form of a moveable clamping jaw 134 is depicted. As shown, first end 156 includes a plurality of clamping teeth 190 for enhanced securement of a first end of the test specimen S. Moveable clamping jaw 134 may be employed in conjunction with a stationary clamping jaw 32, of the type shown in FIG. 3, to form another form of test specimen clamping mechanism 30. In operation, biasing means 36, which may be a pair of coil springs, urges stationary clamping jaw 32 away from moveable clamping jaw 134 to enable a test specimen S to easily be inserted therebetween. At least one test specimen clamping screw 38 may be provided for securing stationary clamping jaw 32 to moveable clamping jaw 134. As may be appreciated, stationary clamping jaw 32 may also be provided with a plurality of clamping teeth (not shown) for further enhanced securement of a first end of the test specimen S.

Figure 4B:
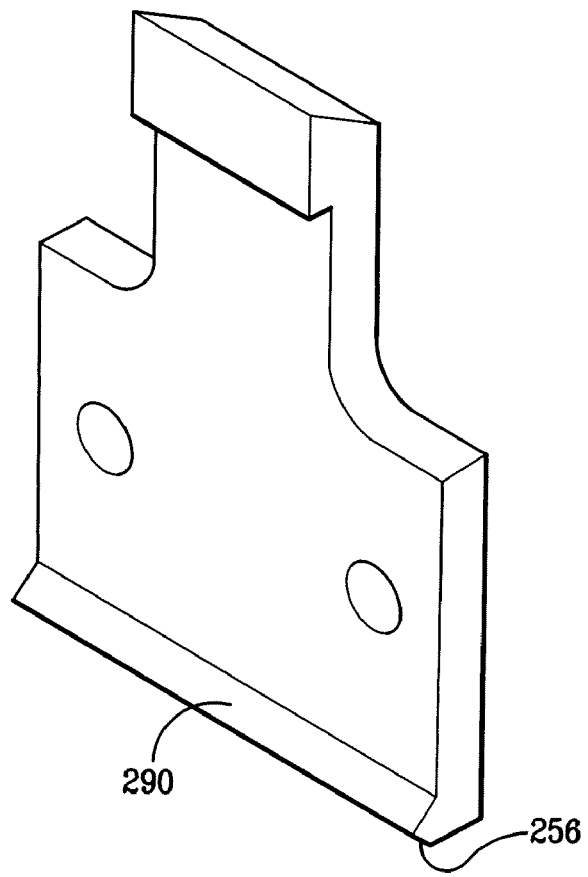
FIG. 4B shows still another form of a movable moveable clamping jaw of a specimen clamping mechanism for use in an apparatus for evaluating the peel adhesion of a test specimen to a substrate, as disclosed herein.

Referring now to FIG. 4B, yet another form of a movable moveable clamping jaw 234 of a specimen clamping mechanism 30 for use in an apparatus 10 for evaluating the peel adhesion of a test specimen S to a substrate T is shown. As shown, first end 256 includes a clamping boss 290 for enhanced securement of a first end of the test specimen S. Moveable clamping jaw 234 may be employed in conjunction with a stationary clamping jaw 32, of the type shown in FIG. 3, to form a test specimen clamping mechanism 30. In operation, biasing means 36, which may be a pair of coil springs, urges stationary clamping jaw 32 away from moveable clamping jaw 234 to enable a test specimen S to easily be inserted therebetween. At least one test specimen clamping screw 38 may be provided for securing stationary clamping jaw 32 to moveable clamping jaw 234.

Referring now to FIGS. 5A and 5B, a substrate clamping plate 48 is depicted. FIG. 5A shows a top perspective view of substrate clamping plate 48, while FIG. 5B shows a bottom perspective view of substrate clamping plate 48. As shown, substrate clamping plate 48 has a smooth top surface 55 and a knurled bottom surface finish 155 for contacting and securing substrate T to the substrate receiving surface 54 of base plate 40 (see FIG. 2). As described hereinabove with reference to FIG. 2, a plurality of clamping plate screws 50 may be provided for securing substrate clamping plate 48 and substrate T to substrate receiving surface 54 of base plate 50. As may be appreciated by those skilled in the art, knurled surface finish 57 provides for the enhanced clamping of substrate T to the substrate receiving surface 54 of base plate 40. The size of window 52 of clamping plate 48 should not be smaller than the size of a test specimen S. Advantageously, window 52 may be sized as close as possible to the size of test specimen S, so that tissue stretching is minimized during a test. As may be appreciated by those skilled in the art, tissue stretching can have a negative impact on peel adhesion test accuracy.

Pivotable linkage 12 has a first end 60 for connecting to the second end 58 of test specimen clamping mechanism 30 and a second end 62 pivotably mounted to adaptor 16. First end 60 of pivotable linkage 12 may optionally be provided with locking pin 26 for mating with locking orifice 28 of second end 58 of test specimen clamping mechanism 30 to maintain engagement during test. A mounting flange (not shown) may be provided at second end 62 of pivotable linkage 12 for mating with pivot pin 18 of adaptor 16, permitting the pivotable movement desired (see FIG. 2). As may be appreciated, this arrangement enables the source of tensile force F to be applied in a direction substantially normal to the substrate at a point where the test specimen is being peeled therefrom. Pivotable linkage 12 has a length L, which is selected to facilitate the ability to apply a tensile force in a direction substantially normal to the substrate at a point where the test specimen is being peeled. Length L may be from about 6 to about 12 inches or from about 8 to about 10 inches to achieve this ability.

As shown in FIG. 1, adaptor 16 is positioned so as to be in communication with a source of tensile force F, the source of tensile force F provided by tensile test load frame 14. The tensile force F is applied to the adaptor 16 to draw the pivotable linkage 12 and test specimen clamping mechanism 30 away from the base plate 40 and peel the test specimen S away from the substrate T. As may be seen by reference to FIG. 6, the point (or line) of peeling is indicated as P. As may be appreciated, tensile testing machine 80 may provide the source of tensile force. Suitable tensile testing machines having utility herein are available, for example, from Instron Corporation of Norwood Massachusetts. A suitable tensile testing machine is Instron® Model 5542, a test setup component of which is schematically depicted in FIG. 1. As shown in FIG. 1, tensile testing machine 80 includes a load frame 14 having a first end 82 for receiving base plate 40 and a second end 84 for receiving adaptor 16.

To monitor the tensile force applied during a peel adhesion test, means for measuring tensile force 64 is provided. While several measuring means are contemplated for use herein, load cells are preferred. While pneumatic load cells are generally considered where intrinsic safety and hygiene are desired and hydraulic load cells are considered where a source of external power is unavailable, strain gage-based load cells may be used in the apparatus and method disclosed herein. As is known to those skilled in the art, a strain gage-based load cell is a transducer which converts force into a measurable electrical output. The gauges themselves are bonded onto a beam or structural member that deforms when weight is applied. In most cases, four strain gages are used to obtain maximum sensitivity and temperature compensation. Two of the gauges are usually in tension, and two in compression. When a force is applied, the strain changes the electrical resistance of the gauges in proportion to the load. Strain gage load cells offer accuracies from within 0.03% to 0.25% full scale.

As shown in FIG. 1, adaptor 16 is mechanically affixed to load cell 64. The electrical response to the tensile force applied may be continuously monitored on a digital readout, whose calibration may be checked from time to time, and/or recorded through the use of an analog graphing mechanism, microprocessor, or personal computer, utilizing suitable software to analyze the data.

In another form, provided is a method of evaluating the peel adhesion of a test specimen S to a substrate T. The method includes the steps of placing a first surface of the substrate T on a base plate 40 having a surface for receiving the substrate 54, securing the substrate T to the substrate receiving surface 54 of the base plate 40, securing a first end 56 of a test specimen clamping mechanism 30 to a first end of the test specimen S, affixing a first surface of the test specimen S to the second surface of the substrate T, affixing a first end 60 of a pivotable linkage 12 to a second end 58 of the test specimen clamping mechanism 30, the second end 62 of the pivotable linkage 12 pivotably mounted to an adaptor 16, the adaptor 16 in communication with a source of tensile force and applying a tensile force to the adaptor 16 to draw the pivotable linkage 12 and test specimen clamping mechanism 30 away from the base plate 40 and peel the first surface of the test specimen S away from the second surface of the substrate T.

In use, the following procedure may be employed. Test samples with biologics should be stored at about 2-8° C. until the test. Tris buffered saline (TBS) for wetting the tissue is prepared by mixing 200 mM Tris-HCl with 150 mM NaCl and pH adjusted to 7.4 using 0.5 N NaOH. However, other wetting fluid such as saline, distilled water or citrated plasma may also be used. Fresh calf pericardial tissue may be used as the tissue substrate T. As may be appreciated by those skilled in the art, the tissue must be used within roughly seven hours of its receipt, since it is known that pre-frozen tissue samples will not yield reproducible results.

The tensile testing machine 80 may be an Instron® Tensile Tester Model 5544, fit with a 10-N load cell or equivalent. Apparatus components described hereinabove are installed on tensile testing machine 80. The calibration of the Instron® test frame and load cell should be verified. In preparation for testing, the test samples and TBS should be brought to room temperature.

To prepare the tissue substrate T for use in the method and apparatus disclosed herein, a calf heart is selected and the fat tissue carefully removed from the pericardial surface at the interface of the pericardial tissue and the fat tissue. It is recommended not to contaminate the pericardial tissue with the grease from the fat. The pericardial tissue is next removed from heart and cut into the required size. For one form of the apparatus disclosed herein, the pericardial tissue may be cut into a dimension of at least about 2.5"×5.5" and placed onto a plate (e.g. a high density polyethylene (HDPE) plate) having a dimension of about 2"×6". The outer surface of the pericardial tissue should be placed face up, as this will be the contacting surface for the test specimen S. Typically, at least three test tissue substrates T can be prepared from a single calf heart. To keep the tissue substrate T wet, drops of saline solution are applied to the tissue surface. However, it should be noted that the tissue substrate should not be immersed in the solution. It is also a good practice to cover the tissue, without contact, to slow down the drying process. As those skilled in the art may appreciate, tissues with cuts and/or defects on their surfaces should not be used, as such defects may induce errors in the test data to be obtained. Tissue substrates T prepared in the manner herein disclosed should be used within 5 hours.

A test specimen S of the type disclosed in U.S. Patent Application No. 2006/0257458, the contents of which are hereby incorporated by reference for all that they disclose, is one type of specimen that may be employed in the method disclosed herein. To test such a specimen S, the foil protective packaging is removed. The specimen S should be carefully handled to minimize flaking of the biomaterials embedded therein. In handling, it is a good practice to handle the test specimen S with the powder-side facing upward in order to minimize the loss of the coating.

The test specimen S may be cut into a portion having a width of about 0.5" to about 1". The length of the specimen S is not critical and can be 2", 3", 4" or any suitable length. For example, for a 2"×3" sample, the prepared specimen dimension may be 0.67"×3". For a product such as TachoSil®, available from Nycomed of Roskilde, Denmark, a 4.8 cm×4.8 cm product may be cut into a test specimen S having a size of 1.6 cm×4.8 cm (0.63"×1.89"). In certain cases, the specimen may be weighed on an analytical balance before testing to evaluate the coating amount and/or evenness of the coating.

Prior to evaluating a test specimen S, the test specimen S should carefully inspected and specimens noted for bare areas, clumps, uneven surfaces, etc, that might affect performance. If a comparison is made for samples of different widths, the peel strength measurement should be adjusted in accordance therewith. In any event, to avoid inducing uncertainty, it is recommended that specimens of similar size be used in a comparison study.

In preparation for a test, the specimen S is placed into the apparatus as herein described and as shown in FIG. 6. To maintain cleanliness during set-up, the sample preparation and testing areas may be covered with a plastic wrap. An appropriately-sized (2-lb.) load cell may be used. Next, the tensile tester 80 is calibrated. With the safety stop in place, the fixtures of the apparatus disclosed herein are installed while adjusting the crosshead height, as appropriate.

The gauge length and force readings are zeroed, the specimen S and apparatus fixtures installed into the upper grip and the force reading zeroed again. When using an Instron® Model 5542 Tensile Tester, the Instron® Series IX software may be initialized and the "Test" mode selected from the menu. Test conditions may be set as shown in Table 1.

TABLE 1

| Test Conditions | |
| --- | --- |
| Load cell | 2-lb |
| Crosshead speed | 8"/min |
| Maximum travel distance | 5 in |
| Specimen dimension | Manual input |
| Force calculation | Average between two user-selected points. Starting point: when a force of 0.05-lb is first achieved. Ending point: when a force of 0.05-lb is last achieved. If a test specimen displays a force lower than 0.05-lb (an indication of extremely low peel adhesion), a lower force (e.g. 0.01-lb) may be used. |

Next, the tissue substrate T is placed onto a flat surface (such as a dish) to prevent the wetting fluid from flowing to one side. Next, a substrate clamping plate 48, having a window 52, is placed on the tissue substrate T. About 4-ml of TBS may be applied with a syringe onto the tissue substrate T surface in the area framed by window 52.

Immediately thereafter, the specimen S is placed onto the tissue substrate T with the coating side down, touching the tissue substrate T, and a weight immediately applied onto the specimen. The weight may be selected to be 90 grams per inch of length for a specimen S. After a few minutes (e.g., 5 minutes), the weight is removed and the test specimen S, substrate T and associated hardware installed onto the tensile tester 80, while adjusting the crosshead height.

Figure 7:
FIG. 7 shows a typical force-displacement curve obtained from a peel adhesion test of the type herein described.

A check is made to assure that there is no pre-load on the sample and the gauge length zeroed. The test may be started by clicking the "Start" button. FIG. 6 shows a typical specimen S during a peel test. A test may be manually terminated after the sample is completely peeled off from the tissue. Otherwise, the test will automatically stop when the maximum travel distance is reached. Starting and ending points are manually selected to calculate the peel strength. However, the peel strength may also be calculated using two pre-determined displacement points, e.g., calculation starts at displacement 0.5" and ends at displacement 3". FIG. 7 shows a typical force-displacement curve obtained from a peel test of the type herein described. The tested sample may be removed for testing additional samples. Upon completion, the test data may be printed for record purposes.

EXAMPLES

Example 1

Four groups of samples from two manufacturing processing methods, A and B, were provided for testing. The samples were of the type disclosed in U.S. Patent Application No. 2006/0257458. Detailed information regarding the samples is listed in Tables 2 and 3. Upon receipt, the samples were kept at about 4° C. until tested. Fresh calf hearts with pericardial tissues were purchased from a local vendor and used as tissue substrates. In the tables that follow, note that the biological active component of a test specimen (e.g., fibrinogen) is referred to by the acronym "BAC."

TABLE 2

Sample Information

| Process | Sample | Powder Content | | HFE (mL) |
| | | Fibrinogen (mg/cm$^2$) | Thrombin (IU/cm$^2$) | |
|---|---|---|---|---|
| A | Baseline | 5.5 | 50 | 12 |
| | Low BAC2 | 1.5 | 50 | 12 |
| | No BAC2 | 0 | 50 | 12 |
| | 1) All samples were made using Process A with PeTG trays. | | | |
| | 2) BAC2 Powder: J44185D; 0.41 g fibrinogen per g solids | | | |
| | 3) Thrombin Powder: J3315SD; 23.93 IU per mg solids | | | |
| | 4) Sample dimension 2 inch × 4 inch | | | |
| B | Batch # 030405 | N/A | N/A | N/A |
| | 1) These samples were made by process B. The samples are referred to as "Run 2". Due to the process employed, the amount of powder may vary across the sample. Individual samples were not weighed during manufacturing. The samples were made with BAC2 having relatively low fibrinogen "specific activity" 0.254 g fibrinogen by Clauss per g solids. | | | |
| | 2) Sample dimension 2 inch × 3 inch | | | |

TABLE 3

Further Information for Process A Samples

| Sample Number | Sample Description | Fibrinogen Content mg/cm$^2$ | Solid, g | Thrombin Content IU/cm$^2$ | Solid, mg | Sample Allocation |
|---|---|---|---|---|---|---|
| 1 | Baseline | 5.5 | 1.5 | 50 | 237 | Peel Precision |
| 2 | Baseline | 5.5 | 1.5 | 50 | 237 | Peel Precision |
| 3 | Baseline | 5.5 | 1.5 | 50 | 237 | Peel Precision |
| 4 | Baseline | 5.5 | 1.5 | 50 | 237 | Peel Precision |
| 5 | Baseline | 5.5 | 1.5 | 50 | 237 | Peel Precision |
| 6 | Baseline | 5.5 | 1.5 | 50 | 237 | Peel Precision |
| 7 | Baseline | 5.5 | 1.5 | 50 | 237 | Peel Precision |
| 8 | Baseline | 5.5 | 1.5 | 50 | 237 | Peel Precision |
| 11 | Low BAC2 | 1.5 | 0.4 | 50 | 237 | Peel Discrimination |
| 12 | Low BAC2 | 1.5 | 0.4 | 50 | 237 | Peel Discrimination |
| 13 | No BAC2 | 0 | 0 | 50 | 237 | Peel Discrimination |
| 14 | No BAC2 | 0 | 0 | 50 | 237 | Peel Discrimination |

All tests were conducted as described hereinabove. Briefly, the pericardial tissue was removed from the fresh calf hearts. The fatty tissues were removed. Then, the pericardial tissue was cut into a size large enough to hold a test specimen and placed onto a polyethylene plate, with the tissue outer surface facing up. The tissue substrate was kept moist by spraying saline on its surface. Each sample was photographed and then cut to 0.67"×4" test specimens. After about 4-ml tris buffer solution (TBS) (0.2M tris, 0.15M NaCl, pH=7.4) was applied to the tissue substrate surface, a test specimen was placed onto the center portion of the tissue substrate and a constant load, as described hereinabove, was applied to the specimen and maintained for 5 minutes. At the end of 5 minutes, the constant load was removed and the specimen was placed and fixed to a peel test fixture and the test was started. All tests were conducted at room temperature on an Instron® Model 5542 Tensile Tester with a 2-lb load cell. Crosshead speed was set to 8"/min. The peel adhesion strength was calculated between two selected points.

Figure 8:
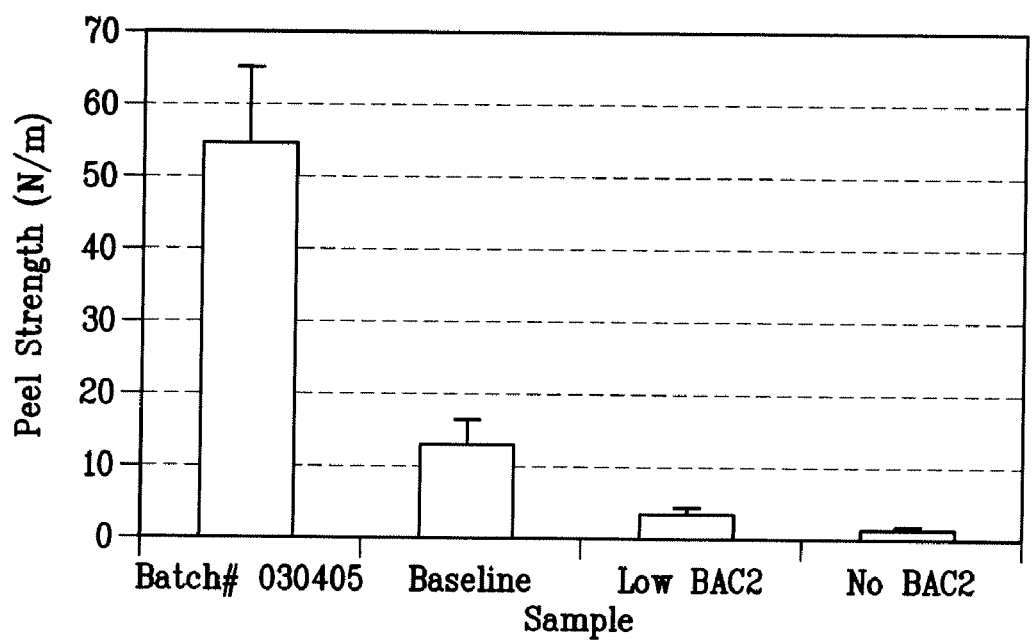
FIG. 8 graphically presents peel strength data for four test samples.
Figure 9:
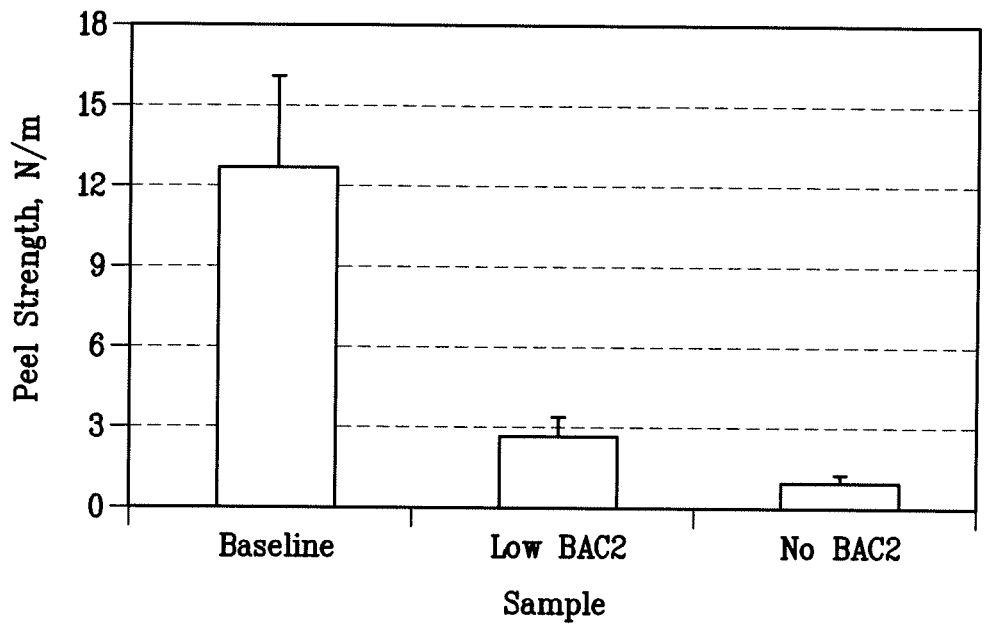
FIG. 9 graphically presents peel strength data for three test samples.
Figure 10:
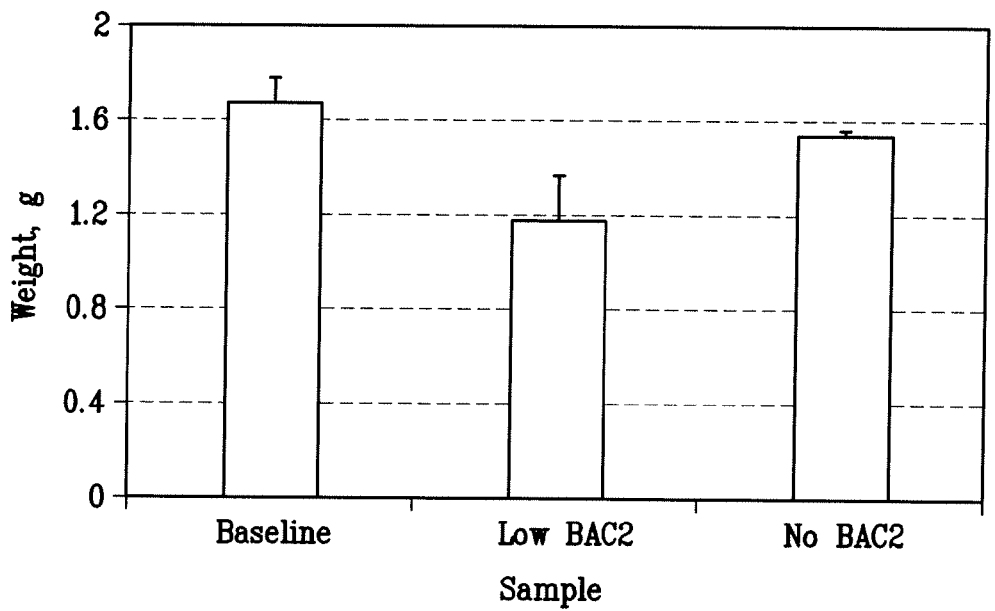
FIG. 10 graphically presents a comparison of sample weights for three test samples.

Tables 4 and 5 present the experimental data of peel strength and their averaged values are given in Table 6, which is also graphically illustrated in FIGS. 8-10. Statistical analysis showed that there were significant differences in peel strength among the four groups of samples. There existed significant differences in peel strength among the Process A samples too. Higher fibrinogen content corresponded with higher peel force. The data also indicated that the peel test method could discriminate the samples even with a very low peel force such as 1-2 N/m. It should be noted that some of the "baseline" Process A samples were non-uniformly coated and that this may have affected the test results.

TABLE 4

Peel Strength Experimental Results for Process A Samples

| Sample # | Description | Sample Weight (g) | Test | Peel force (N/m) |
|---|---|---|---|---|
| 1 | Baseline | 1.768 | 1 | 13.10 |
| | | | 2 | 15.46 |
| | | | 3 | 17.98 |
| 2 | Baseline | 1.523 | 4 | 14.51 |
| | | | 5 | 10.99 |
| | | | 6 | 24.10 |
| 3 | Baseline | 1.748 | 7 | 15.29 |
| | | | 8 | 8.86 |
| | | | 9 | 9.44 |
| 4 | Baseline | 1.732 | 10 | 12.55 |
| | | | 11 | 9.94 |
| | | | 12 | 11.54 |
| 5 | Baseline | 1.660 | 1 | 14.78 |
| | | | 2 | 14.55 |
| | | | 3 | 13.02 |
| 6 | Baseline | 1.567 | 4 | 12.62 |
| | | | 5 | 7.50 |
| | | | 6 | 15.32 |
| 11 | Low BAC2 | 1.306 | 7 | 2.153 |
| | | | 8 | 3.056 |
| | | | 9 | 1.829 |
| 13 | No BAC2 | 1.151 | 10 | 1.061 |
| | | | 11 | 1.089 |
| | | | 12 | 1.512 |
| 7 | Baseline | 1.421 | 1 | 14.07 |
| | | | 2 | 7.66 |
| | | | 3 | 10.61 |
| 8 | Baseline | 1.719 | 4 | 13.14 |
| | | | 5 | 10.39 |
| | | | 6 | 14.88 |
| 12 | Low BAC2 | 0.973 | 7 | 3.111 |
| | | | 8 | 1.803 |
| | | | 9 | 3.066 |
| 14 | No BAC2 | 1.093 | 10 | 0.71 |
| | | | 11 | 1.129 |
| | | | 12 | 0.947 |
| 1 | Baseline | 1.637 | 1 | 13.38 |
| | | | 2 | 11.51 |
| | | | 3 | 6.16 |
| 2 | Baseline | 1.709 | 4 | 8.71 |
| | | | 5 | 11.60 |
| | | | 6 | 12.81 |
| 11 | Low BAC2 | 1.253 | 7 | 3.041 |
| | | | 8 | 3.768 |
| | | | 9 | 2.207 |
| 13 | No BAC2 | 1.088 | 10 | 0.877 |
| | | | 11 | 1.015 |
| | | | 12 | 1.013 |

TABLE 5

Peel Strength Experimental Results for Process B Samples

| Sample # | Test | Peel force (N/m) |
|---|---|---|
| 60 | 1 | 45.97 |
|  | 2 | 53.57 |
|  | 3 | 56.87 |
| 95 | 4 | 53.05 |
|  | 5 | 58.22 |
|  | 6 | 56.51 |
| 65 | 7 | 40.29 |
|  | 8 | 53.31 |
|  | 9 | 57.84 |
| 96 | 1 | 59.11 |
|  | 2 | 67.02 |
|  | 3 | 59.31 |
| 91 | 4 | 83.20 |
|  | 5 | 38.92 |
|  | 6 | 52.79 |
| 90 | 7 | 33.95 |
|  | 8 | 44.51 |
|  | 9 | 55.38 |
| 86 | 1 | 50.45 |
|  | 2 | 48.14 |
|  | 3 | 64.86 |
| 87 | 4 | 52.24 |
|  | 5 | 49.89 |
|  | 6 | 74.01 |

TABLE 6

Averaged Test Data

| Sample | Sample Weight (g) | | | Peel Strength (N/m) | | |
|---|---|---|---|---|---|---|
|  | No. of Tests | Average | SD | No. of Tests | Average | SD |
| Baseline | 10 | 1.649 | 0.112 | 30 | 12.55 | 3.51 |
| Low BAC2 | 3 | 1.177 | 0.179 | 9 | 2.67 | 0.69 |
| No BAC2 | 3 | 1.111 | 0.035 | 9 | 1.04 | 0.22 |
| Batch 030405 | N/A | N/A | N/A | 24 | 54.56 | 10.79 |

Although the samples by Process B had higher strength than those produced by Process A, a direct comparison cannot be made between the two process methods for the following reasons. The Process A samples used in this study were made at a time when the process and formulation had not been optimized and some samples, e.g., 1, 3, and 5 had areas of non-uniform powder coating. Moreover, the fibrinogen content of the samples was not adjusted to account for any losses incurred during the manufacturing process.

As demonstrated, the peel test method disclosed herein can be effectively used to evaluate adhesion strength. As shown, there were significant differences in peel strength among the four groups of samples. For Process A samples, a higher fibrinogen content resulted in a higher peel strength.

Example 2

Three groups of 4"×4" samples of the type disclosed in U.S. Patent Application No. 2006/0257458 were provided for testing. Their detailed information is listed in Table 7. Upon receipt, the samples were kept at about 4° C. until the testing date. Fresh calf hearts with pericardial tissues were purchased from a local vendor and used as test substrates.

TABLE 7

Sample Information

| Run No. | Group | Level of Active Component | Active Component mg/cm$^2$ Fibrinogen | IU/cm$^2$ Thrombin | Post Treatment |
|---|---|---|---|---|---|
| 170 | Baseline | Baseline | 6.7 | 75 | No |
| 172 | Low powder | Low | 2.5 | 25 | No |
| 169 | Baseline heated | Baseline | 6.7 | 75 | Heated at 96° C. for 24 hours to inactivate proteins |

All tests were conducted as described hereinabove. Briefly, the pericardial tissue was removed from the fresh calf hearts. The fatty tissues were removed. Then, the pericardial tissue was cut into a size large enough to hold a test specimen and placed onto a polyethylene plate, with the tissue outer surface facing up. The tissue substrate was kept moist by spraying saline on its surface. Each sample was photographed and then cut to 0.67"×4" test specimens. After about 4-ml tris buffer solution (TBS) (0.2M tris, 0.15M NaCl, pH 7.4) was applied to the tissue substrate surface, a test specimen was placed onto the center portion of the tissue substrate and a constant load, as described hereinabove, was applied to the specimen and maintained for 5 minutes. At the end of 5 minutes, the constant load was removed and the specimen was placed and fixed to a peel test fixture and the test was started. All tests were conducted at room temperature on an Instron® Model 5542 Tensile Tester with a 2-lb load cell. Crosshead speed was set to 8"/min. The peel adhesion strength was calculated between two selected points.

Figure 11:
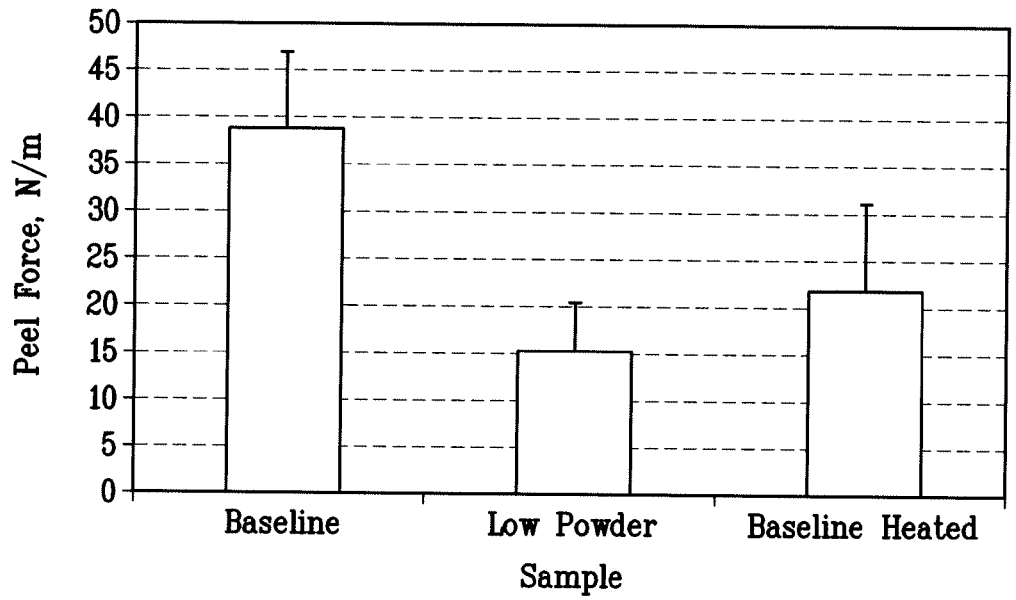
FIG. 11 graphically presents peel strength data for three test samples.
Figure 12:
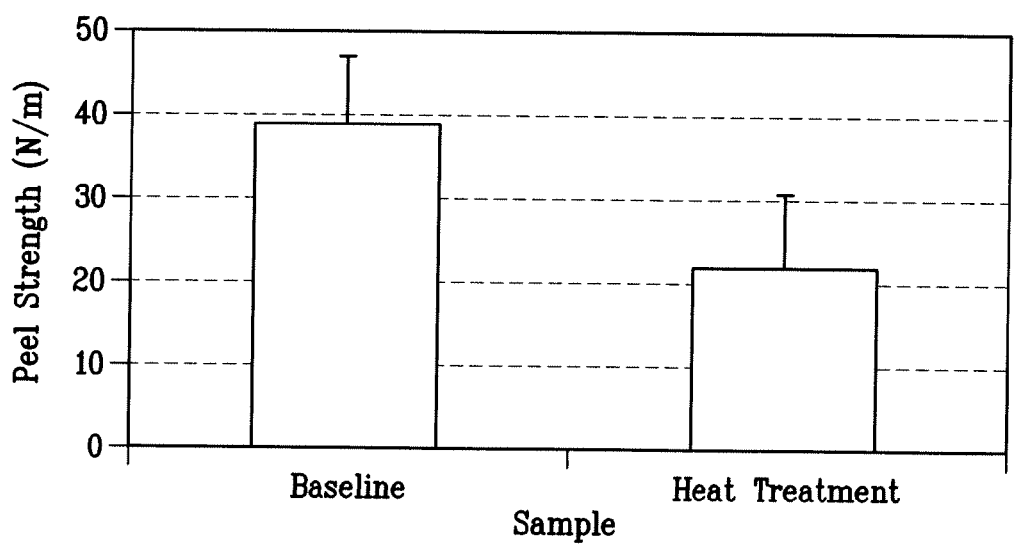
FIG. 12 graphically presents peel strength data showing the impact of heat treatment on peel strength for a pair of test samples.
Figure 13:
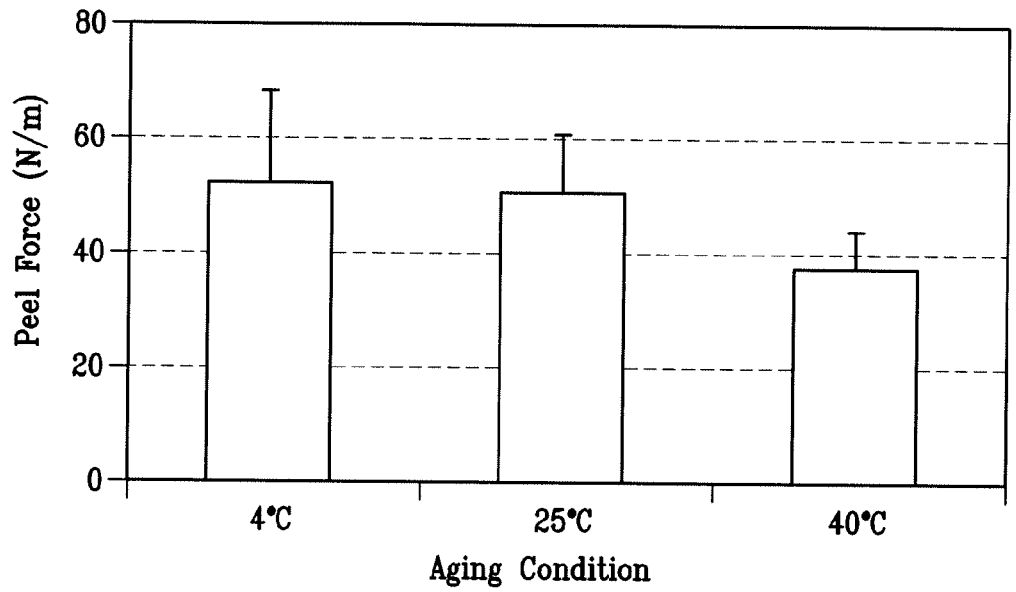
FIG. 13 graphically presents the effect of aging condition on peel strength.
Figure 14:
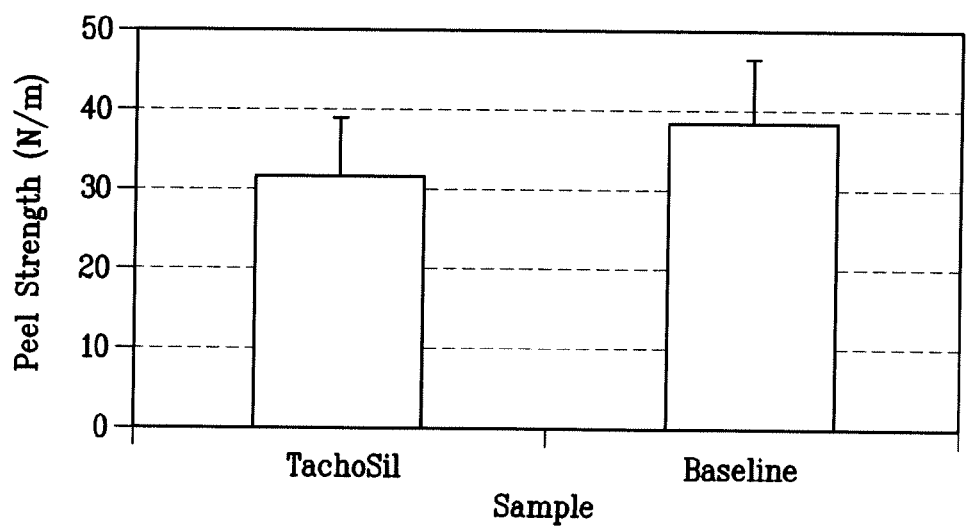
FIG. 14 graphically presents peel strength data for a pair of test samples.

Table 8 presents the experimental data of peel strength with their averaged values. FIG. 11 graphically compares the peel strength of three sample groups and indicates differences exist among them. Moreover, statistical analysis showed that there were significant differences in peel strength among three groups of samples (p<0.01). Compared to the baseline sample, the sample with low powder had significant lower peel strength. Heating the baseline sample at 96° C. for 24 hours significantly decreased its peel strength (see FIG. 12). There were no significant differences between the heated baseline sample and the low powder sample. Inspection of the testing samples indicated that there were some variations in sample coating uniformity, which may have contributed to the variation in testing data.

TABLE 8

Peel Strength Experimental Results

| Sample | Test | Peel force (N/m) | |
|---|---|---|---|
|  |  | Raw data | Mean ± SD |
| Baseline | 1 | 40.14 | 38.84 ± 8.23 |
|  | 2 | 50.75 |  |
|  | 3 | 26.05 |  |
|  | 4 | 41.28 |  |
|  | 5 | 34.14 |  |
|  | 6 | 40.69 |  |
| Low powder | 7 | 24.83 | 15.30 ± 5.24 |
|  | 8 | 9.47 |  |
|  | 9 | 15.64 |  |
|  | 10 | 15.76 |  |
|  | 11 | 12.03 |  |
|  | 12 | 14.10 |  |

TABLE 8-continued

Peel Strength Experimental Results

| | | Peel force (N/m) | |
|---|---|---|---|
| Sample | Test | Raw data | Mean ± SD |
| Baseline heated | 13 | 14.63 | 21.78 ± 9.24 |
| | 14 | 16.31 | |
| | 15 | 16.92 | |
| | 16 | 15.58 | |
| | 17 | 34.99 | |
| | 18 | 32.22 | |

Example 3

The six samples (4"×4") were received in the sealed packages that had been subjected to three stability aging conditions for 6 months: 4° C., 25° C./60% and 40° C./75%. Two samples were received at each condition. The samples were cut into a test specimen of 4"×0.67" for peel test. Fresh calf pericardial tissue was used as adhesion substrate. All tests were conducted at room temperature on an Instron 5544 tester with a 2-lb load cell. Experimental results are summarized in Table 9 and graphically illustrated in FIG. 13. Statistical analysis indicated that the samples stored at 40° C./75%RH for 6 months had significant lower peel strength than those stored at 4° C. and 25° C./60%RH. However, there were no significant differences in peel strength between the samples stored at 4° C. and 25° C./60%RH for 6 months.

TABLE 9

Experimental Data for Peel Force (N/m)

| | 4° C. | | 25° C./60% | | 40° C./75% | |
|---|---|---|---|---|---|---|
| Test run | Peel Force | Sample # | Peel Force | Sample # | Peel Force | Sample # |
| 1 | 41.52 | 044 | 49.16 | 0198 | 36.1 | 0174 |
| 2 | 47.47 | | 45.97 | | 47 | |
| 3 | 44.65 | | 57.32 | | 41.88 | |
| 4 | 46.41 | | 75.28 | | 29.86 | |
| 5 | 51.51 | | 43.57 | | 37.63 | |
| 6 | 47.97 | | 48.4 | | 38.03 | |
| 7 | 60.86 | 038 | 51.61 | 0186 | 29.47 | 0158 |
| 8 | 45.03 | | 56.46 | | 33.73 | |
| 9 | 97.45 | | 37.41 | | 51.04 | |
| 10 | 55.35 | | 48.87 | | 44.16 | |
| 11 | 32.04 | | 37.86 | | 31.87 | |
| 12 | 40.48 | | 46.41 | | 32.8 | |
| Average | 50.9 | | 49.86 | | 37.8 | |
| SD | 16.38 | | 10.08 | | 6.94 | |

Example 4

Two 4.8 cm×4.8 cm TachoSil® samples (Lot #10283369) in sealed packages were used to conduct a peel force evaluation. The samples were kept at about 4° C. prior to testing. Fresh calf hearts with pericardial tissues were purchased from a local vendor and used as test substrates. A peel test was conducted for the TachoSil® samples and the results were compared with the baseline data in Table 8. Experimental results are summarized in Table 10 and graphically illustrated in FIG. 14.

TABLE 10

Peel Strength Experimental Results

| | | Peel force (N/m) | |
|---|---|---|---|
| Sample | Test | Raw data | Mean ± SD |
| TachoSil® | 1 | 33.87 | 30.80 ± 8.14 |
| | 2 | 30.50 | |
| | 3 | 45.52 | |
| | 4 | 25.17 | |
| | 5 | 26.08 | |
| | 6 | 23.67 | |

All patents, test procedures, and other documents cited herein, including priority documents, are fully incorporated by reference to the extent such disclosure is not inconsistent with this invention and for all jurisdictions in which such incorporation is permitted.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the invention, including all features which would be treated as equivalents thereof by those skilled in the art to which the invention pertains.

What is claimed is:

1. An apparatus for evaluating the peel adhesion of a test specimen to a substrate, comprising:
   (a) a base plate having a surface for receiving the substrate;
   (b) a substrate clamping plate for securing the substrate to said substrate receiving surface of said base plate, wherein said clamping plate comprises a first surface and a second surface, said first surface having a knurled surface finish;
   (c) a test specimen clamping mechanism, said test specimen clamping mechanism having a first end for securing a first end of the test specimen thereto and a second end; and
   (d) a pivotable linkage, said pivotable linkage having a first end for connecting to said second end of said test specimen clamping mechanism and a second end pivotably mounted to an adaptor, said adaptor in communication with a source of tensile force,
   wherein the source of tensile force is applied through or via said adaptor to draw said pivotable linkage and test specimen clamping mechanism away from said base plate and peel the test specimen away from the substrate.

2. The apparatus of claim 1, wherein the source of tensile force is applied in a direction substantially normal to the substrate at a point where the test specimen is being peeled therefrom.

3. The apparatus of claim 1, further comprising means for measuring the tensile force applied.

4. The apparatus of claim 3, wherein said tensile force measuring means is a load cell.

5. The apparatus of claim 4, wherein said adaptor is mechanically affixed to said load cell.

6. The apparatus of claim 1, wherein said test specimen clamping mechanism comprises a stationary clamping jaw and a moveable clamping jaw.

7. The apparatus of claim 6, wherein said moveable clamping jaw of said test specimen clamping mechanism includes a plurality of clamping teeth at said first end thereof.

8. The apparatus of claim 6, wherein said moveable clamping jaw of said test specimen clamping mechanism includes a clamping boss at said first end thereof.

9. The apparatus of claim 1, further comprising a tensile testing machine comprising a load frame having a first end for receiving said base plate and a second end for receiving said adaptor.

10. A method of evaluating the peel adhesion of a test specimen to a substrate, comprising the steps of:
   (a) placing a first surface of the substrate on a base plate having a surface for receiving the substrate;
   (b) placing a substrate having a first surface with a knurled finish directly over a portion of the substrate and securing the substrate clamping plate to the substrate receiving surface of the plate;
   (c) securing a first end of a test specimen clamping mechanism to a first end of the test specimen;
   (d) affixing a first surface of the test specimen to the second surface of the substrate;
   (e) affixing a first end of a pivotable linkage to a second end of the test specimen clamping mechanism, the second end of the pivotable linkage pivotably mounted to an adaptor, the adaptor in communication with a source of tensile force; and
   (f) applying a tensile force through or via the adaptor to draw the pivotable linkage and test specimen clamping mechanism away from the base plate and peel the first surface of the test specimen away from the second surface of the substrate.

11. The method of claim 10, wherein said step of applying a tensile force is conducted so as to apply the tensile force in a direction substantially normal to the substrate at a point where the test specimen is being peeled therefrom.

12. The method of claim 10, further comprising the step of measuring the tensile force applied.

13. The method of claim 12, wherein said step of measuring the tensile force utilizes a load cell.

14. The method of claim 13, wherein the adaptor is mechanically affixed to the load cell.

15. The method of claim 10, wherein the test specimen clamping mechanism comprises a stationary clamping jaw and a moveable clamping jaw.

16. The method of claim 15, wherein the moveable clamping jaw of the test specimen clamping mechanism includes a plurality of clamping teeth at the first end thereof.

17. The method of claim 15, wherein the moveable clamping jaw of the test specimen clamping mechanism includes a clamping boss at the first end thereof.

* * * * *